United States Patent
Watanabe et al.

(10) Patent No.: US 7,635,333 B2
(45) Date of Patent: Dec. 22, 2009

(54) ULTRASOUND DIAGNOSTIC APPARATUS

(75) Inventors: Tetsuo Watanabe, Mitaka (JP); Akifumi Ohtake, Mitaka (JP); Takaya Uno, Mitaka (JP)

(73) Assignee: Aloka Co., Ltd., Tokyo (JP)

( * ) Notice: Subject to any disclaimer, the term of this patent is extended or adjusted under 35 U.S.C. 154(b) by 453 days.

(21) Appl. No.: 11/104,238

(22) Filed: Apr. 12, 2005

(65) Prior Publication Data
US 2005/0251037 A1 Nov. 10, 2005

(30) Foreign Application Priority Data
Apr. 21, 2004 (JP) ............................. 2004-125145

(51) Int. Cl.
*A61B 8/00* (2006.01)
(52) U.S. Cl. .................. 600/437; 600/443; 600/450
(58) Field of Classification Search ............... 600/437, 600/443, 407, 450; 345/545, 531, 530; 382/305, 382/128
See application file for complete search history.

(56) References Cited

U.S. PATENT DOCUMENTS

| | | | |
|---|---|---|---|
| 4,846,188 A | 7/1989 | Yoshioka | |
| 5,152,290 A * | 10/1992 | Freeland | 600/443 |
| 5,976,088 A * | 11/1999 | Urbano et al. | 600/443 |
| 6,162,176 A * | 12/2000 | Washburn et al. | 600/454 |
| 6,312,382 B1 * | 11/2001 | Mucci et al. | 600/437 |
| 6,503,203 B1 * | 1/2003 | Rafter et al. | 600/458 |
| 2002/0036641 A1 | 3/2002 | Amemiya | |

FOREIGN PATENT DOCUMENTS

| | | |
|---|---|---|
| JP | 2063447 | 3/1990 |
| JP | 6269455 | 9/1994 |
| JP | 11-137550 | 5/1999 |
| JP | 2000-271120 | 10/2000 |
| JP | 2002-085409 | 3/2002 |

* cited by examiner

*Primary Examiner*—Eric F Winakur
*Assistant Examiner*—Katherine L Fernandez
(74) *Attorney, Agent, or Firm*—William L. Androlia; H. Henry Koda

(57) ABSTRACT

An ultrasound diagnosis apparatus comprises a cine-memory for temporarily storing a frame line obtained by transmitting and receiving ultrasound. In a stress echo test, the storage region of the cine-memory is divided into the same number of segments as the number of capturing processes (i.e. the number of scenes). Each segment is used as a ring-buffer, and one or a plurality of frame blocks (one or a plurality of moving images) are stored in the corresponding segment in each capturing process. Prior to execution of a plurality of capturing processes, the number of heart beats indicative of the data amount which can be stored in each segment is obtained and the information is then provided to a user.

14 Claims, 5 Drawing Sheets

ULTRASOUND DIAGNOSTIC APPARATUS

BACKGROUND OF THE INVENTION

1. Field of the Invention

The present invention relates to an ultrasound diagnostic apparatus, and more particularly to a technique for storing data in a memory section.

2. Description of Related Art

Most ultrasound (ultrasonic) diagnostic apparatuses used in the medical field include a cine-memory which is formed as a ring buffer or a temporary storage. A cine-memory stores data obtained through the transmission and reception of ultrasound. An ultrasound image is formed based on the data read from the cine-memory and the ultrasonic image is then displayed on a display device. Normally, the cine-memory stores data in units of one frame or one line. Here, one line corresponds to one ultrasound beam and one frame corresponds to one scan plane or one ultrasound image. A cine-memory generally has a storage capacity allowing storage of multiple numbers of frames obtained in time sequence. In a cine-memory, the newest input data overwrites the oldest data which is already stored in the memory, and this process is repeated.

When a freeze operation is performed by a user during real-time diagnosis, transmission and reception of ultrasound are stopped. In such a frozen state, it is possible to read data stored in the cine-memory and reproduce the data as a still image or a moving image. Because a cine-memory is generally stored on a volatile storage medium, the data content of the cine-memory is lost when the power of an ultrasound diagnosis apparatus is turned off. Further, due to the data overwriting as described above, data on the cine-memory is also lost sequentially. It is therefore necessary to save important data stored in the cine-memory. Accordingly, the data stored in a cine-memory is transferred to a non-volatile storage medium such as a hard disk or the like.

In a stress echo test, a patient is subjected to increasing stress in a series of steps by a physical or pharmaceutical method. Specifically, a test which is performed for one patient at one time includes a plurality of "stages", and ultrasound diagnosis is performed from a plurality of "views" in each stage. More specifically, a "scene" is determined by a combination of a stage and a view, and a moving image obtained in ultrasound diagnosis (namely, in a capturing process) which is performed for each scene is stored. In this case, the image is stored in units of one heart beat, for example. After moving images for all the necessary scenes are captured and stored, the user selects a plurality of scenes for which images are to be reproduced. Then, a plurality of moving images corresponding to a plurality of scenes which are selected by the user are simultaneously reproduced in parallel to each other. The user can then compare and observe these moving images, whereby diagnosis of a disease concerning an organ such as the heart can be performed.

Japanese Patent Laid-Open Publication No. Hei 6-269455 describes an ultrasound diagnosis apparatus in which data obtained over a plurality of successive heart beats is transferred from a memory section to an external storage device. Japanese Patent Laid-Open Publication No. Hei 2-63447 describes an ultrasound diagnosis apparatus including a memory section which functions as a cine-memory. The storage region of the memory section is divided into two regions, each of which is used as a ring-buffer. Japanese Patent Laid-Open Publication No. Hei 2-63447, however, does not describe that the number into which the storage region is divided is variable in accordance with different ultrasound tests or a diagnostic states.

In each capturing process in a stress echo test, when a plurality of frames which are obtained are sequentially stored in a cine-memory, the stored data which was obtained in the past is to be erased by overwriting by new data, unless overwriting is prohibited with respect to the stored data. However, if prohibition of overwrite is set with regard to a great amount of data stored on the cine-memory in the preceding capturing processes, sufficient storage region cannot be secured in the subsequent capturing processes, thereby impairing completion of all processes of the stress echo test. Stated simply, the cine-memory runs out of a free space. On the other hand, when the amount of data stored in the preceding capturing process is reduced so as to secure a sufficient free space for the subsequent capturing processes, it is not possible to make effective use of the overall storage capacity over the entire stress echo test. In each capturing process, it is desirable to store, in addition to a moving image for a specific heart beat which is to be actually used for evaluation, a moving image for other heart beats as backup. However, conventionally, it is not possible for a user to appropriately determine the number of heart beats as the units of moving images to be stored in each capturing process. In a stress echo test, it is difficult to strictly predict the data amount to be obtained at the start of the test, because the heart rate changes with the change of stages.

SUMMARY OF THE INVENTION

The present invention advantageously enables appropriate storage of data obtained in each capturing process.

Another advantage of the present invention is effective use of the storage capacity of a whole cine-memory.

A still further advantage of the present invention is the ability to provide a user with a reference value of the data amount which can be captured in each capturing process.

(1) In accordance with one aspect, an ultrasound diagnosis apparatus of the present invention comprises a memory section for temporarily storing a plurality of frames obtained by transmitting and receiving ultrasound; a setting section for setting the number of capturing processes in a predetermined ultrasound test; a dividing section for dividing a storage region of the memory section into a plurality of segments; and a control section for performing control to cause each of the plurality of segments to function as a ring-buffer, thereby allowing one or a plurality of frame blocks obtained in each capturing process in the predetermined ultrasound test to be stored in a corresponding one of the segments.

With the above structure, the storage region of the memory section is divided into a plurality of segments, and one or a plurality of frame blocks (corresponding to one or a plurality of moving images) obtained in each capturing process are stored in each segment. In this manner, the storage region exclusively used for each capturing process is secured in advance as a ring-buffer (a temporary storage), so that one or a plurality of frame blocks obtained in each capturing process can be stored reliably. With this process, the conventional problems of the memory running out of free space, or an undesirably large free storage space being left in the capturing process at the final stage of the predetermined ultrasound test, can be avoided.

Preferably, the memory section is a cine-memory, which is physically composed of one or a plurality of storage devices. The memory section may alternatively be formed by a high speed accessible non-volatile storage device (for example, a hard disk). The memory section may be provided before or after, or upstream or downstream of, (or inside) a scan converter. Namely, each frame constituting the frame block may be either a transmitting/receiving frame or a display frame. The predetermined ultrasound test is preferably a stress echo test. While the number of capturing processes is generally determined by a user, it may be provided as external information or determined automatically as a default value. The number of segments is determined in accordance with the number of capturing processes which is variably set. Namely, the storage capacity of each segment basically depends on the number of capturing processes. While each segment preferably has the same storage capacity (a fixed length method), the storage capacity of the respective segments may be varied in accordance with the predicted change in the cardiac cycle (a variable length method). In any case, it is desirable to divide and control the segments so that shortage or excess of a free storage region is not caused toward the end of a test and also moving images which were already captured can be reliably maintained. When a plurality of frame blocks (a plurality of moving images) to be stored are specified in each capturing process, these frame blocks are preferably arranged in time sequence, but they may also exist discretely on the time axis. Because each segment has a ring-buffer structure, typically, the newest input frame overwrites the oldest frame which is already stored. When one or a plurality of frame blocks are specified by a capturing command such as a freeze operation, writing of data with respect to the segment as a whole which stores these specified frame blocks is subsequently prohibited. Alternatively, overwriting may be prohibited only with respect to the one or plurality of frame blocks which are specified. While an ultrasound diagnosis apparatus of the present invention is particularly preferable for use in a stress echo test, it may also be used for other ultrasound tests.

Preferably, the ultrasound diagnosis apparatus may further comprise an estimation section for estimating information concerning the number of frame blocks which can be stored in each of the segments, and a providing section for providing the information concerning the number of frame blocks which can be stored in each of the segments to a user. With this structure, by providing the above-described information to a user, the user can obtain a reference value indicating how many number of frame blocks can be stored in each capturing process. Consequently, the user can select one or a plurality of frame blocks which are more important or have higher degree of priority from the clinical viewpoint, while recognizing the above-described reference value. It is also possible to use the provided information to determine whether or not the number of capturing processes should be reset. Preferably, each frame block corresponds to moving images for one heart beat (or several heart beats), and in this case, the number of heart beats which can be stored in each segment is supplied as the above-described information.

Preferably, the ultrasound diagnosis apparatus may further comprise a detection section for detecting a biological signal indicative of the cardiac cycle, and each of the frame blocks is specified based on the biological signal and corresponds to moving images for n heart beats, where n=1, 2, 3, . . . (where n is an integer greater than or equal to 1), and the estimation section estimates, as the information concerning the number of frame blocks which can be stored in each of the segments, the number of heart beats which can be captured, based on the storage capacity of each of the segments and a predicted data amount for the n heart beats. With this structure, the amount of moving images, i.e. the number of heart beats, which can be captured in each segment can be predicted from the relationship between the storage capacity of each segment and the predicted data amount for n heart beats. Preferably, n=1.

Preferably, the storage capacity of each of the segments is specified by dividing a whole storage capacity in the memory section by the number of capturing processes, the predicted size or volume of the data for n heart beats is specified based on a heart rate, a frame rate, and a data amount per frame which are obtained from the biological signal, and the number of heart beats which can be captured is specified by dividing the storage capacity of each of the segments by the predicted data volume for n heart beats. The frame rate is either a transmitting/receiving frame rate or a display frame rate. The whole storage capacity of the memory section corresponds to the whole storage region which can be allocated to a plurality of capturing processes, and the memory section may further include a storage region other than that can be allocated to a plurality of capturing processes as described above.

Preferably, the predetermined ultrasound test is a stress echo test in which ultrasound diagnostic is performed with a plurality of views in each of stages while a level of load (stress) with respect to a living body is being switched stepwise, and the number of capturing process is defined by the number of stages and the number of views. Namely, the number of capturing processes corresponds to the number of scenes.

Preferably, the size of each segment is uniformly set. Preferably, the size of each segment is variably set. When the storage capacity of each segment is uniform, segment dividing and data control is facilitated. When the storage capacity of each segment is individually set, on the other hand, allocation of the storage capacity can be performed reasonably in accordance with a variation of the heart rate. Preferably, each frame stored in the memory section is a display frame. Preferably, each frame stored in the memory section is a transmitting/receiving frame.

Here, the whole storage region in the memory section may be divided into a plurality of segments, or the entire storage region of the memory section is first segmented into a main storage region and a margin storage region and then the main storage region may be divided into a plurality of segments. When a certain segment runs out of a free region as an exceptional case, the shortage may be compensated by the margin storage region. The division of the segment may be a physical dividing of the memory or a logical dividing. When the memory is logically divided, in a physical sense, one segment is defined as a set of a plurality of partial regions provided discretely on the memory.

(2) In accordance with another aspect, an ultrasound diagnosis apparatus which can be used in a stress echo test, of the present invention comprises a memory section for temporarily storing a plurality of frames obtained by transmitting and receiving ultrasound; a process number setting section for setting the number of capturing processes in the stress echo test; a segment setting section for setting a plurality of segments with respect to the memory section in accordance with the number of capturing processes; a storage control section for storing data obtained in each of the capturing processes in the stress echo test with respect to each of the segments; and a providing section for providing information concerning a data amount which can be stored in each of the segments to a user. It is desirable that the information concerning the data amount which can be stored in each segment is provided to a user prior to execution of a plurality of capturing process.

Preferably, the information concerning a data amount which can be stored in each of the segments is the number of heart beats. Preferably, the number of heart beats is calculated using, as a basis, the cardiac cycle of a living body at rest or before being stressed. Namely, a reference value is calculated using, as a basis, the cardiac cycle where the heart beats at a low rate. Consequently, even when the load (stress) of a living body is increased to thereby shorten the cardiac cycle, data corresponding to a greater number of heart beats than in the above-described reference value can be stored.

BRIEF DESCRIPTION OF THE DRAWINGS

Preferred embodiments of the present invention will be described in detail with reference to the following drawings, wherein.

DETAILED DESCRIPTION OF PREFERRED EMBODIMENTS

Figure 1:
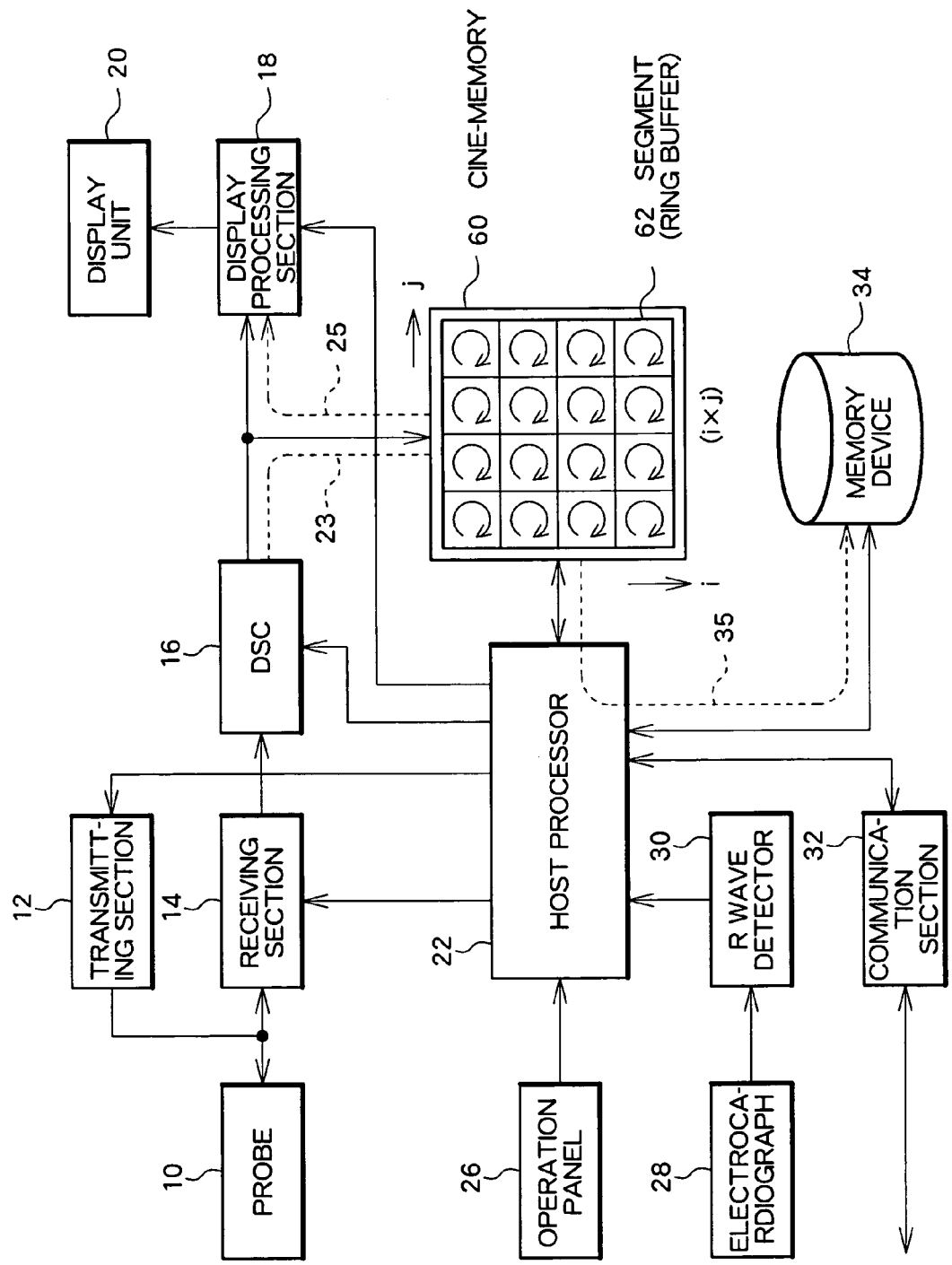
FIG. 1 is a block diagram showing an ultrasound diagnosis apparatus according to a preferred embodiment of the present invention.

Preferred embodiments of the present invention will be described in detail with reference to the drawings. FIG. 1 shows a first preferred embodiment of an ultrasound diagnosis apparatus according to the present invention. Referring to FIG. 1, a whole structure of the ultrasound diagnosis apparatus is shown. While this ultrasound diagnosis apparatus is particularly suitable for use in a stress echo test, the apparatus may also be used for other tests.

A probe 10 transmits and receives ultrasound. More specifically, the probe 10 includes an array transducer (not shown) which is composed of a plurality of transducer elements, and generates an ultrasound beam by means of the array transducer. The ultrasound beam is electronically scanned. The electronic scanning methods include, for example, an electronic linear scanning method, an electronic sector scanning method, and so on. A 2D array transducer may be provided in the probe 10. A 2D array transducer is composed of a plurality of transducer elements arranged two-dimensionally, and can be used for capturing three-dimensional echo data. The probe 10 may be used in contact with a surface of a living body or may be inserted into a body cavity of a living body.

A transmitting section 12 functions as a transmitting beam former, and supplies a plurality of transmitting signals to a plurality of transducer elements within the probe. A receiving section 14 functions as a receiving beam former and performs processes such as phase adjustment and summation with respect to a plurality of receiving signals output from a plurality of transducer elements within the probe 10. The receiving signals thus processed (echo data) are output to a DSC (digital scan converter) 16 via a signal processor which is not shown.

The DSC 16 has a coordinate conversion function, a data interpolation function, or the like. The DSC 16 forms a B mode image (a two-dimensional tomographic image) as an ultrasound image based on the echo data. More specifically, a frame line (a frame data line) obtained by transmitting and receiving ultrasound is input to the DSC 16 in time sequence. Each of frames constituting the frame line is a transmitting/receiving frame which is composed of a plurality of beam data items. The DSC 16 performs an image forming process based on the input frame line, and outputs a frame line constituting a moving image, that is a display frame line, in time sequence. The frame line thus output is then supplied to a display processing section 18. Here, the frame line may be transferred from the DSC 16 to the display processing section 18 via a cine-memory 60 which will be described below.

The display processing section 18 has an image synthesizing function or the like. The display processing section 18 processes input image data and outputs the processed result to a display unit 20, where a moving image (or a still image) is displayed. An ultrasound image includes, for example, a two-dimensional tomographic image, a two-dimensional blood flow image, and a three-dimensional image.

In the example shown in FIG. 1, the cine-memory 60 is provided downstream of or after the DSC 16. In the present embodiment, the cine-memory 16 is composed of one or a plurality of memory devices, and temporarily stores the frame line output from the DSC 16 in time sequence. In a normal operation mode, as in the conventional art, the cine-memory 60 as a whole functions as a single ring buffer. Therefore, the cine-memory 60 continuously stores a series of frames starting from the frame which was stored at a time point predetermined time before the current time to the newest frame. When a new frame is input to the cine-memory 60, the new frame overwrites the oldest frame, and this process is repeated.

According to the present embodiment, in a stress echo test, prior to execution of the first capturing process, the cine-memory 60 is divided into a plurality of segments 62 (see FIG. 1) in accordance with the number of capturing processes, namely the number of scenes, which is required for a stress echo test with regard to a specific patient. Specifically, the whole storage region in the cine-memory 60 is divided into a plurality of storage sub-regions, each of which functions as a temporary storage or a ring buffer. Each segment 62 stores one or a plurality of frame blocks obtained in the corresponding capturing process. As will be described below, when the last capturing process of a stress echo test is completed, one or a plurality of frame blocks obtained in each capturing process are stored in each segment 62 on the cine-memory 60.

More specifically, in a stress echo test, i stages are set and j views are further set in each stage. Here, i is an integer number which is 2 or greater, and j is an integer number which is 1 or greater, preferably 2 or greater. The values of i and j are designated manually or set automatically depending on a patient and a purpose of the test. The stage indicates a load (stress) level placed to a patient or a state of load (stress). The view indicates an observation direction with respect to an organ such as the heart, for example. With the change of the position and direction of the probe 10 on a living body surface, the observation direction also changes. For a whole stress echo test, i×j scenes are defined and a capturing process is performed for each scene. When i is 4 and j is 4, for example, 16 scenes are to be defined. In this case, the whole storage region of the cine-memory 60 is divided into sixteen corresponding to the number of scenes (i.e. the number of capturing processes), and each divided region constitutes the above-described segment 62.

Alternatively, it is also possible that the whole storage region of the cine-memory 60 is segmented into a main storage region and a storage sub-region, of which only the main storage region is further divided into a plurality of segments 62, rather than dividing the whole storage region of the cine-memory 60 into a plurality of segments 62 as described above. In this case, the storage sub-region functions as a margin region which compensates for a shortage of the free space of a segment. While in the present embodiment, the segments 62 have the same storage capacity, the segment storage capacity may be variable for each stage as necessary, taking consideration of the fact that the heart rate (the number of heart beats within a predetermined time period) varies for each stage.

A host processor 22 performs operation control of each of the elements shown in FIG. 1. In particular, the host processor 22 controls writing and reading of data in the cine-memory 60, and also performs segment diving and segment control with respect to the cine-memory 60 in a stress echo test. As will be described below, prior to a stress echo test, once the number of scenes is specified, the host processor 22 performs a process for providing information (the heart rate in the present embodiment) indicative of the amount of moving images which can be stored in each segment to a user.

A memory device 34, in addition to the cine-memory 60 described above, is also connected to the host processor 22. The memory device 34 is formed by a non-volatile memory device such as a hard disk, for example. The cine-memory 60 is composed of one or a plurality of volatile memory devices (RAMs, for example), as described above. In order to save the data stored in the cine-memory 60, the host processor 22 operates such that the data stored in each segment 62 on the cine-memory 60 is read and transferred to the memory device 34, as indicated by numeral 35. Here, data is transferred in units of one frame block corresponding to one heart rate.

With such a configuration, it is possible that a rank indicative of the degree of significance or priority is assigned to each frame block and the transfer timing (or overwrite permission timing) of frame blocks is controlled in accordance with the rank. For example, it may be configured that a frame block with high degree of significance is transferred immediately whereas a frame block with low degree of significance is transferred when a plurality of capturing processes are completed and consequently the load of the host processor 22 is reduced.

An operation panel 26 is connected to the host processor 22. The operation panel 26 includes a keyboard, a track ball, or the like. A user can use the operation panel 26 to set the number of stages i and the number of views j as desired, in accordance with a patient, a symptom, a purpose of the test, and so on. A user can also use the operation panel 26 to input a capturing command for fixing one or a plurality of frame blocks on each segment 62. The capturing command is generated by operation of a freeze switch, for example.

An electrocardiograph 28 is a device for measuring an electrocardiographic signal concerning a living body as a patient. An electrocardiographic signal output from the electrocardiograph 28 is supplied to an R wave detector 30. The R wave detector 30 detects an R wave in an electrocardiographic signal and outputs the detected signal to the host processor 22. The host processor 22 then recognizes each heart beat, and also specifies and controls the frame blocks, based on the detected signal. A communication section 32 is a module for performing data communication between the host processor 22 and an external device. For example, the apparatus may be configured such that the data stored in the cine-memory 60 or the memory device 34 is transferred, via the host processor 22 and the communication section 32, and further via the network, to an external device (such as an image processing device and an image server, for example).

As described above, a frame line output from the DSC 16 is supplied in time sequence and sequentially stored in the cine-memory as indicated by numeral 23. In a stress echo test, a frame line (a moving image) obtained in each capturing process is stored in each segment 62. More specifically, one or a plurality of frame blocks are stored in each segment 62. In the present embodiment, one frame block corresponds to one heart beat. Alternatively, one frame block corresponds to two or other number of heart beats. The moving image stored in the cine-memory 60 is transferred from the cine-memory 60 to the display processing section 18 for display in the display unit 20 as required, as indicated by numeral 25. In this case, the R wave can be used as a synchronization signal to achieve simultaneous and parallel loop reproduction of a plurality of moving images. For example, when image diagnosis is performed in the last stage of a stress echo test, a plurality of scenes are designated and loop reproduction of a plurality of moving images concerning the plurality of scenes which are designated is simultaneously performed, so that diagnosis can be performed while these moving images are being compared and observed. Here, of a plurality of frame blocks (i.e. a plurality of moving images) stored in each segment 62, one moving image having the highest rank assigned becomes the object of loop reproduction. However, a plurality of moving images stored in each segment 62 as a whole may be subjected to loop reproduction.

Figure 2:
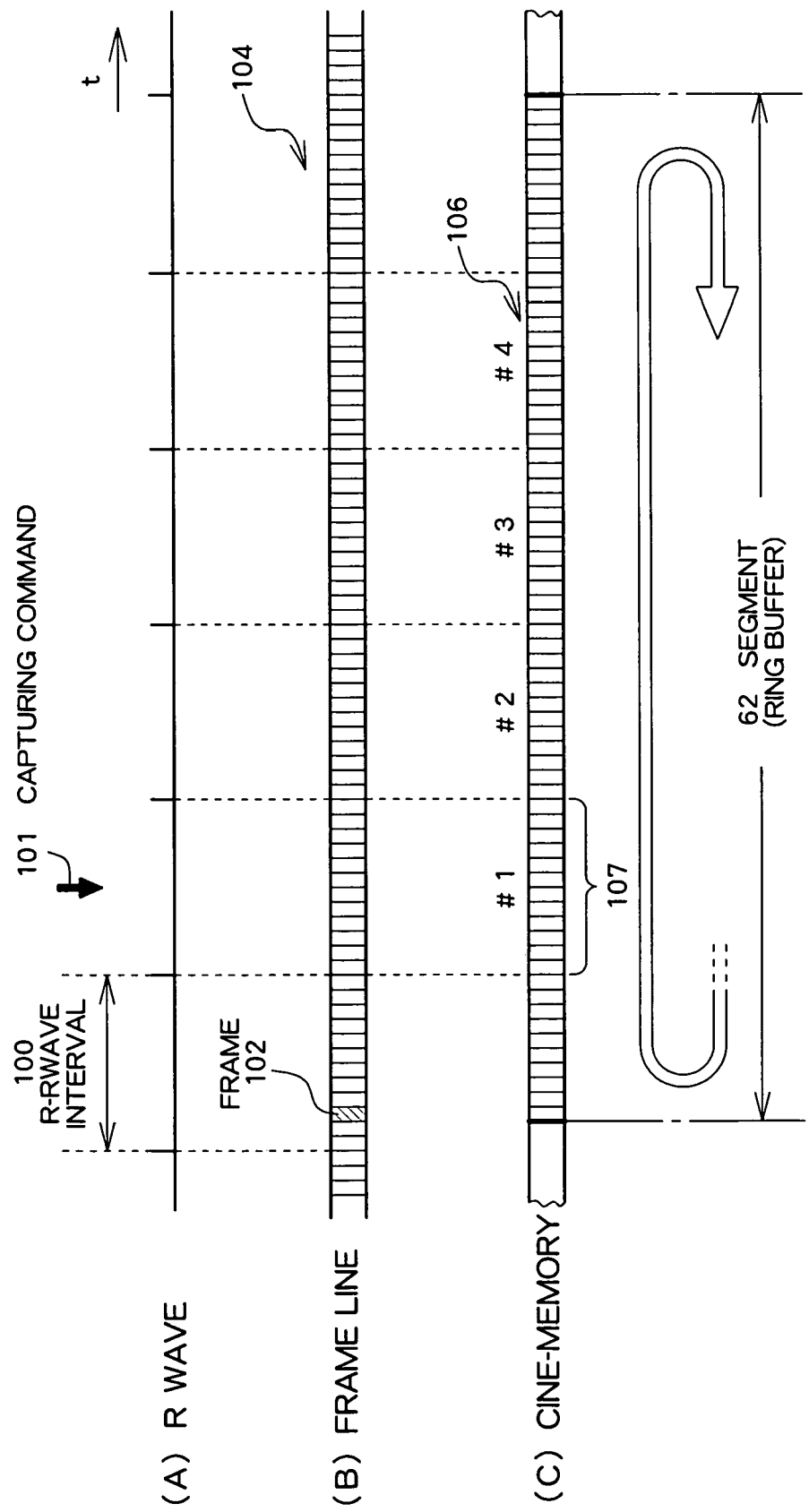
FIG. 2 is a view for explaining storage of a frame line with respect to a cine-memory provided in the ultrasound diagnosis apparatus shown in FIG. 1.

FIG. 2 shows an operation of the cine-memory 60 in a stress echo test. Specifically, Indicator(A) shows an electrocardiographic signal, particularly one heart beat defined by an R wave interval 100. Indicator(B) shows a frame line 104 to be input to the cine-memory. The frame line 104 is composed of a plurality of frames 102 arranged in time sequence. Indicator(C) shows the content of a single segment 62 in the cine-memory. As described above, the segment 62 constitutes a single ring buffer and stores each frame sequentially input in the order of address in the segment 62. When writing with regard to the last address is completed, writing is performed from the first address. In this case, the newest frame overwrites the oldest frame in the segment 62.

In the process of sequentially storing a plurality of frames in the segment 62, when a capturing command 101 is supplied by a freeze operation of a user or the like, one or a plurality of frame blocks are frozen (specifically, fixed) on the segment 62 with the timing at which the capturing command is input being used as a start point. In FIG. 2, numeral 106 represents a block set. In the shown example, the block set 106 is composed of a plurality of frame blocks indicated by #1 to #4 which are arranged in time sequence. In this example, each frame set 107 corresponds to a moving image for one heart beat. For example, during execution of a certain capturing process, when the content which should be noted clinically is recognized in the process of observation of a B mode image (moving image) displayed on a display screen, a capturing command 101 is supplied by a user. Then, using this timing as a start point, the content of the segment 62 associated with the capturing process is fixed. More specifically, further writing with respect to the segment 62 is prohibited, whereby the clinically important image is preserved.

As described above, according to the present embodiment, prior to execution of a plurality of capturing processes, a plurality of segments corresponding to a plurality of capturing processes are established. Then, a plurality of capturing processes are sequentially performed in order. In each capturing process, a plurality of frames are sequentially written with respect to a corresponding segment which is previously provided. When a capturing command is input by a user, with the input timing being used as a start point, the content of the corresponding segment is fixed. In such a state, one or a plurality of moving images which should be saved remain stored in the corresponding segment and further writing with respect to the corresponding segment is prohibited. Consequently, one or a plurality of moving images which should be saved can reliably be stored in each capturing process. Accordingly, it is possible to prevent the problem of the memory running out of a free memory space for storing a moving image which should be captured or that the storage region allocated to each capturing process is reduced due to an excess free space. Thus, efficient data storage with regard to a cine-memory can be achieved.

In the present embodiment, at the point in time where a plurality of frame blocks 107 are fixed on the segment 62 shown in FIG. 2, a rank is assigned to each frame block by a user. Each frame block 107 is processed according to the priority corresponding to the assigned rank. For example, a frame block to which the highest rank is assigned is controlled such that it is displayed first at the time of loop reproduction. Consequently, loop reproduction of this frame block is repeated unless the reproduction target is switched.

Figure 3:
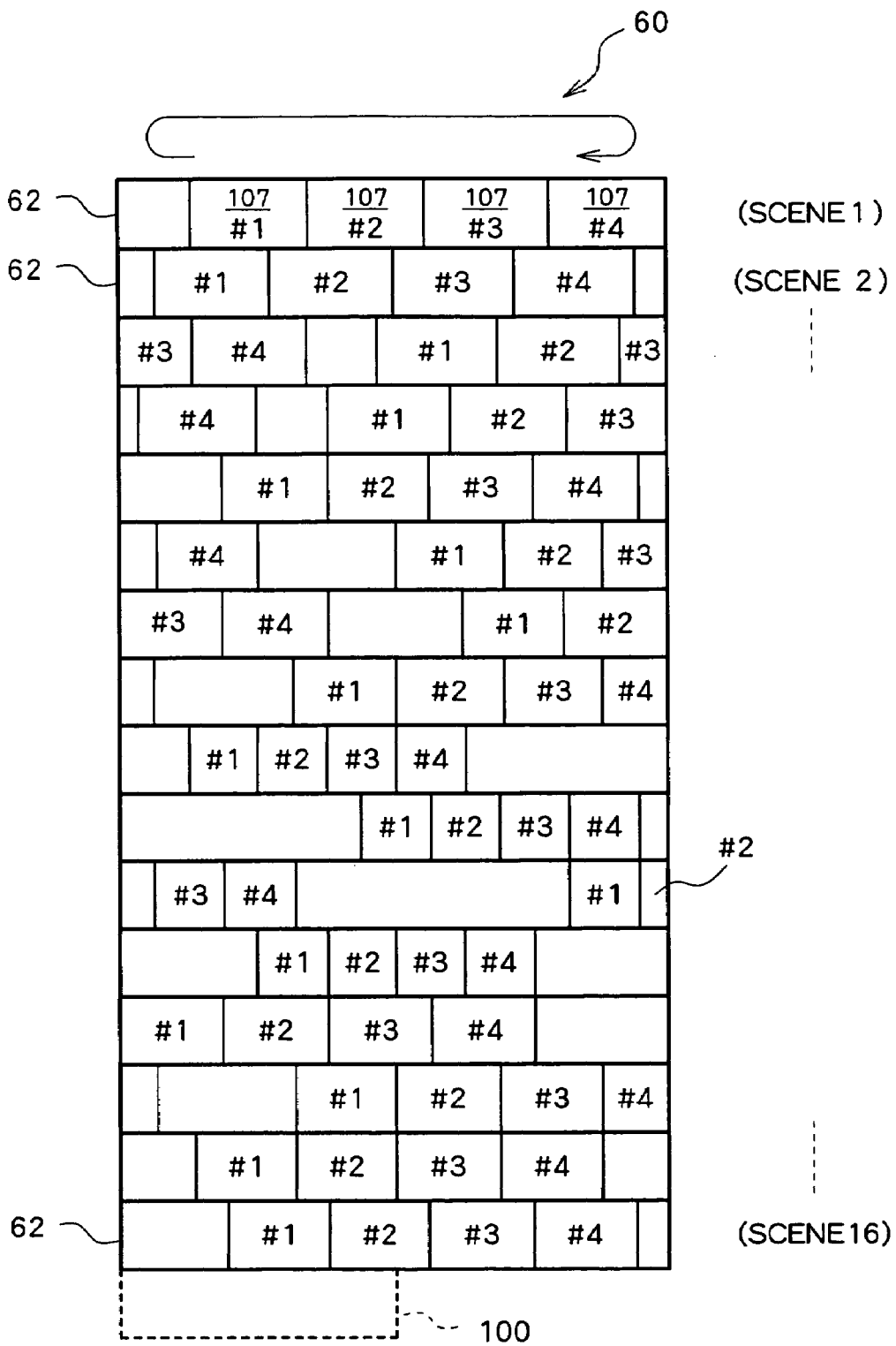
FIG. 3 is a view showing a storage state of a plurality of segments which are set on the cine-memory.

FIG. 3 illustrates the content of the cine-memory 60. A plurality of segments 62 are logically set in the cine-memory 60, and a plurality of frame blocks 107 are stored in the corresponding segment in each capturing process. In the example shown in FIG. 3, 16 scenes are defined as the number of stages is 4 and the number of views is 4. In this example, at least (or normally speaking) 4 frame blocks 107 or moving images #1 to #4 corresponding to 4 heart beats can be stored for each scene. In each segment 62, the storage content is frozen with the timing at which a capturing command as a freeze operation is supplied being used as a start point. Consequently, the sequence of the moving images #1 to #4 (particularly the position of the first moving image #1) varies among different segments.

As shown in FIG. 3, a margin region 100 may be set in the cine-memory 60. Specifically, when the moving images corresponding to 4 heart beats cannot be stored in any segment, a part or all of the margin region 100 may be additionally used as a part of the storage region of the segment. Incidentally, because the number of heart beats per unit time, namely the heart rate, increases as the load (stress) placed on a living body increases, the data size of the frame block varies for different stages.

Figure 4:
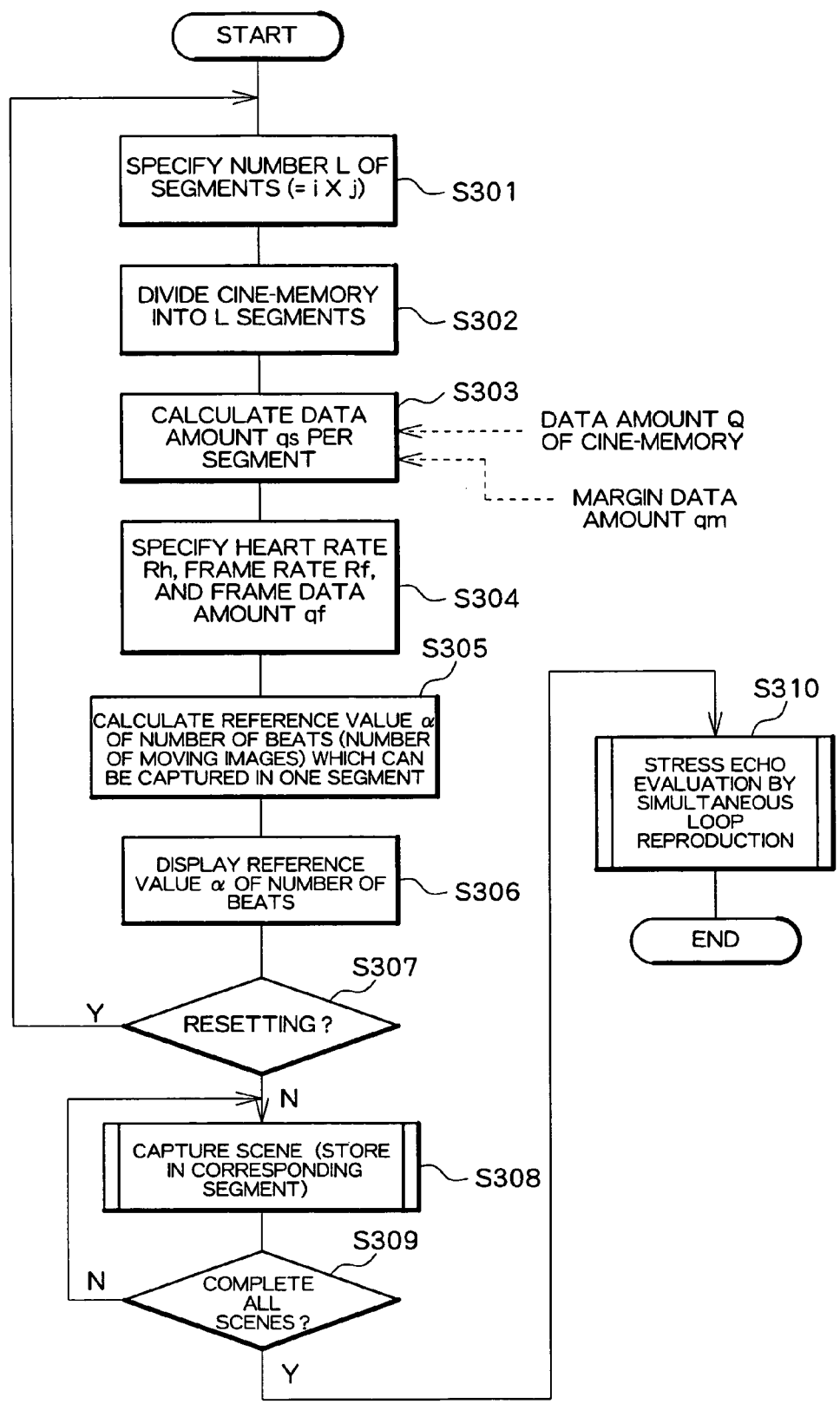
FIG. 4 is a flowchart showing an example operation of the ultrasound diagnosis apparatus shown in FIG. 1.

Referring to FIG. 4, the operation of the structure shown in FIG. 1 will be described. FIG. 4 shows the process content in a stress echo test. First, the number L of segments is specified at step S301. More specifically, the number i of stages and the number j of views are specified by a user, whereby the number L of segments is defined by calculating L=i×j. The number L of segments is 16, for example. Then, as shown in FIGS. 1 and 3, the cine-memory 60 is divided into L segments at step S302. Such dividing of segments makes it possible to secure the memory space for each capturing process or each scene in advance.

At step S303, the data capacity qs per segment is calculated. Specifically, the data capacity qs is obtained as a result of dividing the whole data capacity Q of the cine-memory by the number L of segments, and it is possible to pre-exclude a predetermined margin capacity qm as described above and then calculate the data capacity qs for each segment.

At step S304, the current heart rate Rh is calculated based on an electrocardiographic signal, and the frame rate Rf under the current operating conditions is also recognized. Here, the frame rate Rf refers to a frame rate concerning the frame line output from the DSC. However, when the cine-memory is provided upstream of or before the DSC 16 as will be described below with reference to FIG. 5, the frame rate Rf corresponds to the transmitting/receiving frame rate. Further, the data amount qf for each frame is also specified at step S304. By calculating Rh×Rf×qf, the volume of data captured corresponding to one heart beat or the data volume constituting one frame block is specified.

At step S305, a reference value α of the number of heart beats (the number of beats) which can be captured in one segment is calculated based on the calculation results at steps S303 and S304. More specifically, the value α can be obtained as an integer in the solution obtained by dividing the data capacity qs in one segment by the data amount per heart beat (Rh×Rf×qf).

Accordingly, the heart rate Rh which is recognized at step S304 is desirably a low rate obtained at rest before a living body is stressed. By calculating the above-described value α in such a state, the minimum reference value of the number of moving images which can be stored in one segment can be obtained. When an error in which the even data amount corresponding to only one heart beat cannot be stored in one segment occurs, it is possible to perform resetting of the number of segments at step S307 as will be described below or perform a predetermined error process.

At step S306, the information α calculated at step S305 is provided to the user. More specifically, the information α is transmitted from the host processor 22 to the display processing section 22 and is then displayed on the display screen as a numeral value. The user determines whether or not resetting of the number L of segments should be performed at S307. When resetting is determined, the processes starting from the step S301 are repeated.

After the initial setting and the initial process as described above are completed, each capturing process is sequentially performed at step S308. More specifically, at step S308, the current scene number is specified and the segment corresponding to the scene is specified. With the specified segment functioning as a ring buffer, the storage content in the corresponding segment is frozen at the timing when a capturing command is obtained. Namely, one or a plurality of moving images corresponding to one or a plurality of heart beats are stored on the corresponding segment.

After the moving images corresponding to one or a plurality of heart beats are stored within the segment, a rank may be assigned to each moving image as described above or, alternatively, no special designation may be performed. In either case, a moving image which is required for image diagnosis (a stress echo evaluation) which will be performed later is stored in each segment whose content is frozen.

At step S309, it is determined whether or not the capturing process has been performed for all scenes. If it is determined, at step S301, that the capturing process is completed for all of the scenes, a plurality of scenes are designated among the above-described 16 scenes, and simultaneous loop reproduction of a plurality of moving images corresponding to these scenes is performed with R waves synchronized with each other. Normally, one moving image is loop-reproduced with respect to one scene. However, it is also possible to perform loop reproduction of a set of moving images composed of a plurality of moving images with regard to one scene. A physician, as a user, can diagnose a disease concerning a living body by comparing and observing these moving images.

According to the above embodiment, it is possible to preset the required number of ring buffers on a cine-memory, in accordance with the number of capturing processes included in a stress echo test. When such information is set in advance, the corresponding ring buffer can be used in each capturing process for reliably storing necessary data. It is therefore possible to make an effective use of the whole storage capacity of the cine-memory and also to appropriately allocate the storage capacity to each capturing process. According to the above embodiment, at the time of initial setting, the information concerning a reference value of the number of heart beats which can be captured in one capturing process is supplied to the user. The user can then perform an operation in each capturing process in an appropriate manner based on the stored information. It is generally recognized that a conventional stress echo test places a great burden on the patient being examined. The present embodiment advantageously greatly reduces the likelihood that it will be necessary to repeat a stress echo test.

In the embodiment shown in FIG. 1, the cine-memory 60 is provided downstream of the DSC 16, and a frame line which has been subjected to an image forming process and output from the DSC 16 is stored in the cine-memory 60. However, a cine-memory 60A may be provided upstream of the DSC 16, as will be described below.

Figure 5:
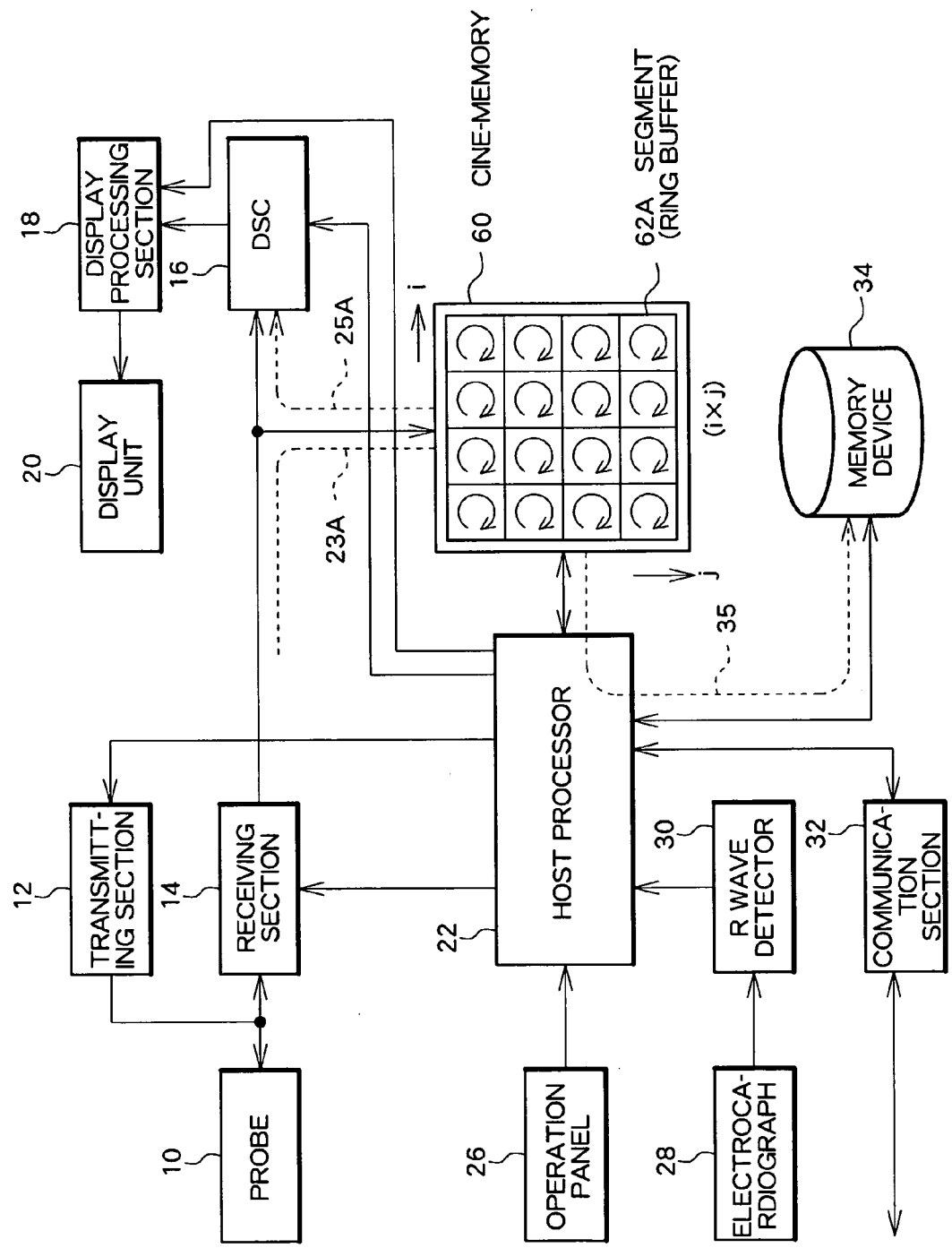
FIG. 5 is a block diagram showing a structure of an ultrasound diagnosis apparatus according to another embodiment of the present invention.

FIG. 5 shows a structure according to another embodiment of the present invention. In FIG. 5, the same elements as those in FIG. 1 are denoted by the same numerals. A frame line output from the receiving section 14 is sequentially stored in the cine-memory 60A as indicated by numeral 23A. Then, a frame line read from the cine-memory 60A is supplied to the DSC 16. The DSC 16 performs a process such as coordinates conversion with respect to the input frame data to generate a frame line composed of a plurality of display frames, which are then output to the display processing section 18. With the structure shown in FIG. 5, the cine-memory 60A is divided into a plurality of segments 62A at the first stage of the stress echo test. Each segment 62A stores a frame line obtained in the associated capturing process. Here, each of frames constituting the frame line is a transmitting/receiving frame, which is composed of a plurality of beam data items.

In the embodiments shown in FIGS. 1 and 5, the overall storage capacity of the cine-memory is divided into a plurality of segments in accordance with the number of capturing processes, and these segments have a uniform storage capacity. However, because the heart rate varies with the progress of a stress echo test, as described above, the storage capacity of the segments may be individually varied for each stage, based on the variation tendency of the heart rate. In this case, it is similarly desirable that the information α as shown in FIG. 4 is provided to the user. It is also desirable that the storage capacity of each segment is individually set such that the number of heart beats which can be captured in each segment is unified to the greatest possible extent.

Although in the embodiments shown in FIGS. 1 and 5, the cine-memory is formed by a storage device such as RAM, other storage devices may also be used as a cine-memory. For example, a hard disk with respect to which high-speed writing and reading is performed may be used. In such a case, a plurality of segments are similarly set in a storage region in such a hard disk which functions as a cine-memory, as described above, and each segment functions as a temporary storage or a ring buffer. Further, in a cine-memory, the segments may be memory portions which are physically consecutive to each other or memory portions which are logically consecutive to each other. In the latter case, a plurality of portions which are dispersed on the memory are controlled as a single segment as a whole. However, consecutive storage regions are generally used as one segment.

While the preferred embodiments of the present invention have been described using specific terms, such description is for illustrative purposes only, and it is to be understood that changes and variations may be made without departing from the spirit or scope of the appended claims.

What is claimed is:

1. An ultrasound diagnosis apparatus comprising:
   a memory section configured to temporarily store a plurality of frames obtained by transmitting and receiving ultrasound;
   a setting section configured to set the number of capturing processes in a predetermined ultrasound test, the number of capturing processes being set prior to a first one of said capturing processes;
   a dividing section configured to divide a storage region of the memory section into a plurality of segments prior to said first one of said capturing processes; and
   a control section configured to perform control to cause each of the plurality of segments to function as a ring-buffer, thereby allowing one or a plurality of frame blocks obtained in each capturing process in the predetermined ultrasound test to be stored in a corresponding one of each of the plurality of the segments; wherein
   the storage region of the memory section is divided in accordance with the number of capturing processes;
   the number of segments is the same as the number of capturing process;
   each segment is a storage region exclusively used for each capturing process.

2. An ultrasound diagnosis apparatus according to claim 1, further composing:
   an estimation section configured to estimate information concerning the number of frame blocks which can be stored in each of the segments; and
   a providing section configured to provide the information concerning the number of frame blocks which can be stored in each of the segments to a user.

3. An ultrasound diagnosis apparatus according to claim 2, further comprising:
   a detection section configured to detect a biological signal indicative of a cardiac cycle,
   wherein each of the frame blocks is specified based on the biological signal and corresponds to a moving image for n heart beats, where n is a positive integer other than 0, and
   the estimation section estimates, as the information concerning the number of frame blocks which can be stored in each of the segments, the number of heart beats which can be captured, based on the storage capacity of each of the segments and a predicted volume of data for the n heart beats.

4. An ultrasound diagnosis apparatus according to claim 3, wherein
   the storage capacity of each of the segments is specified by dividing a whole storage capacity in the memory section by the number of capturing processes,
   the predicted volume of data for n heart beats is specified based on a heart rate, a frame rate, and a data amount per frame which are obtained from the biological signal, and
   the number of heart beats which can be captured is specified by dividing the storage capacity of each of the segments by the predicted volume of data for n heart beats.

5. An ultrasound diagnosis apparatus according to claim 1, wherein
   the predetermined ultrasound test is a stress echo test in which ultrasound diagnostic is performed with a plurality of views in each of stages while a level of stress with respect to a living body is being changed stepwise, and
   the number of capturing processes is defined by the number of stages and the number of views.

6. An ultrasound diagnosis apparatus according to claim 1, wherein the size of each of the segments is uniformly set.

7. An ultrasound diagnosis apparatus according to claim 1, wherein the size of each of the segments is variably set.

8. An ultrasound diagnosis apparatus according to claim 1, wherein each of the frames stored in the memory section is a display frame.

9. An ultrasound diagnosis apparatus according to claim 1, wherein each of the frames stored in the memory section is a transmitting/receiving frame.

10. An ultrasonic diagnostic apparatus according to claim 1, wherein a memory device is provided for storing data transferred from each of the plurality of segments in units of one frame block corresponding to one heart rate.

11. An ultrasonic diagnostic apparatus according to claim 10, further comprising a means for assigning a rank indicative of a degree of significance and transfer timing to each frame block wherein each frame block is transferred from said memory section to said memory device according to said rank assigned to each frame block.

12. An ultrasound diagnosis apparatus which can be used in a stress echo test, comprising:
- a memory section configured to temporarily store a plurality of frames obtained by transmitting and receiving ultrasound;
- a process number setting section configured to set the number of capturing processes in the stress echo test, the number of capturing processes being set prior to a first one of said capturing processes;
- a segment setting section configured to set a plurality of segments with respect to the memory section in accordance with the number of capturing processes prior to a first one of said capturing processes;
- a storage control section configured to store data obtained in each of the capturing processes in the stress echo test with respect to each of the plurality of segments to cause each of said plurality of segments to function as a ring-buffer; and
- a providing section configured to provide information concerning an amount of data which can be stored in each of the plurality of segments for a user; wherein
- the number of segments is the same as the number of capturing processes; and
- each segment is a storage region exclusively used for each capturing process.

13. An ultrasound diagnosis apparatus according to claim 12, wherein
the information concerning an amount of data which can be stored in each of the segments is information identifying a number of heart beats.

14. An ultrasound diagnosis apparatus according to claim 13, wherein
the number of heart beats is calculated using, as a basis, a cardiac cycle of a living body at rest or before the living body is subjected to stress.

* * * * *